United States Patent [19]

Jacobson

[11] Patent Number: 4,483,996
[45] Date of Patent: Nov. 20, 1984

[54] PROCESS FOR PRODUCTION OF OLEFIN OXIDES AND KETONES

[75] Inventor: Stephen E. Jacobson, Morristown, N.J.

[73] Assignee: The Halcon SD Group, Inc., New York, N.Y.

[21] Appl. No.: 468,427

[22] Filed: Feb. 22, 1983

[51] Int. Cl.$^3$ .......................................... C07D 301/03
[52] U.S. Cl. .................................... 549/524; 549/230; 568/365
[58] Field of Search ........................................ 549/524

[56] References Cited

U.S. PATENT DOCUMENTS

| | | | |
|---|---|---|---|
| 3,048,636 | 8/1962 | Grinstead | 260/586 |
| 3,436,409 | 4/1969 | Hill et al. | 549/524 |
| 3,452,047 | 6/1969 | Frye | 260/340.5 |
| 3,479,262 | 11/1969 | MacLean et al. | 204/80 |
| 3,641,067 | 2/1972 | Kruse | 549/524 |
| 4,021,453 | 5/1977 | Brill | 549/524 |
| 4,031,196 | 6/1977 | Leonard | 423/624 |
| 4,146,545 | 3/1979 | Leonard | 549/524 |
| 4,192,814 | 3/1980 | Johnson | 423/111 |
| 4,290,959 | 9/1981 | Barker | 549/524 |

FOREIGN PATENT DOCUMENTS 2255298 7/1975 France .

OTHER PUBLICATIONS

W. Kruse et al., Jour. Org. Chem., vol. 36, No. 8, (1971), pp. 1154–1155.

*Primary Examiner*—Norma S. Milestone
*Attorney, Agent, or Firm*—William C. Long; Riggs T. Stewart; Daniel R. Zirker

[57] ABSTRACT

A process for converting a desired olefin to the corresponding olefin oxide, such as propylene oxide, and/or ketone comprising reacting a mixture of the olefin, thallic oxide, carbon dioxide and water in a substantially organic solvent-free reaction zone; withdrawing a product stream from the reaction zone, the stream comprising the olefin and ketone product; separating and collecting the olefin oxide and ketone product from the stream; contacting the reduced thallous values present in the mixture with molecular oxygen and an effective catalyst to back oxidize the thallous values to their original thallic form; separating and recycling back to the reaction mixture the regenerated thallic values.

21 Claims, No Drawings

PROCESS FOR PRODUCTION OF OLEFIN OXIDES AND KETONES

BACKGROUND OF INVENTION

1. Field of Invention

This invention is related to the oxidation of olefins to their corresponding olefin oxides and ketones and, in particular, is related to the oxidation of propylene by thallic oxide in an aqueous, $CO_2$ rich environment.

2. Description of Prior Art

W. Kruse, et al, *J. Org. Chem.* 30th Vol., pp. 114 ('71) describes the preparation of certain selected epoxides by the oxidation of the corresponding olefin with thallic acetate in weakly solvating media.

U.S. Pat. No. 3,641,067 (issued in 1972 to W. Kruse) also describes the preparation of the epoxide of propylene and isobutylene in an aqueous system by using lower alkyl thallic carboxylates, in the presence of a water-miscible organic solvent and an aliphatic monocarboxylic acid containing from one to four carbon atoms.

French Pat. No. 2,255,298 (issued in 1975 to Societe des Usines Chimiques Rhone-Poulenc) sought to improve the concentration of propylene oxide in the product by a multi-step process of reacting propylene at low temperatures with an aqueous solution having a pH of not greater than six and containing a thallic salt of an aliphatic monocarboxylic acid having from one to four carbon atoms, a carboxylic acid which is miscible with or soluble in water, and a water-miscible organic solvent. (Aliphatic monocarboxylic acids of one to four carbon atoms are specified as being suitable.) The pH of the resulting reaction mixture is next critically adjusted to a value of at least seven and the adjusted solution then heated, with immediate and rapid removal of the propylene oxide formed.

While French Pat. No. 2,255,298 achieves effective results, the careful pH control required in this process is quite costly on an industrial scale.

U.S. Pat. No. 4,021,453 to W. F. Brill discloses a process for preparing epoxides from the corresponding olefins using aryl thallic carboxylates having up to 12 carbon atoms in the presence of an inert polar organic solvent and water and, optionally, in the presence of free aryl carboxylic acids.

U.S. Pat. No. 4,290,959 to R. S. Barker discloses a process for preparing propylene oxide in which propylene is oxidized by means of a thallic salt in the presence of aqueous media containing an alkanoic acid having at least seven carbon atoms and, optionally, in the presence of an organic solvent.

U.S. Pat. Nos. 4,031,196 and 4,146,545 to J. Leonard disclose the use of thallic oxide in the preparation of propylene oxide. In an aqueous alkaline solution having a pH greater than 11.9, thallous isobutyrate is oxidized by air at a temperature within a range from about 90° to about 250° C. to prepare a slurry of thallic oxide from which thallic oxide can be recovered. The alkaline isobutyrate solution can be treated with carbon dioxide under pressure to form an isobutyric acid product which can be solvent extracted from the aqueous system using a hydrophobic solvent as extractant. Gaseous propylene can be bubbled through a liquid reaction mixture containing water, an organic solvent miscible with water and thallic trialkanoate to prepare gaseous propylene oxide. The carbonate salt can be thermally decomposed to regenerate an alkaline metal hydroxide and carbon dioxide. The availability of this preparation of thallic oxide makes feasible the recycling of most of the reaction components. This process is extremely awkward, however, particularly on a large industrial scale, involving many separate operations.

Oxidation of thallous compounds to the thallic state is well known and has been disclosed in a great number of publications and patents. A substantial number of these are disclosed in U.S. Pat. No. 4,192,814.

There has been a long standing need to discover an efficient, economical, process which uses thallic values for the oxidation of olefinic compounds to their corresponding oxides while permitting the efficient and effective back oxidation and recycling of the reduced thallous values to their thallic state for reuse in the process cycle.

It is an object of this invention to provide an improved cyclical process for the oxidation of olefins to their corresponding olefin oxides and ketones by the use of thallic oxide as the oxidizing agent in an organic solvent-free, acid-free medium.

It is another object of this invention to provide an improved olefin oxidizing process which employs thallic oxides as the oxidizing agent that can efficiently and economically subsequently regenerate the thallous values back to the thallic state after the reduction in the olefin oxidizing reaction.

It is still another object of this invention to remove the oxidized olefin products from the reaction mixture without having any significant glycol formation.

It is still another object of the invention to develop a thallous oxidizing catalyst which is compatible with the formed olefin products of the process.

It is still another object of this invention to develop a more catalytically active thallic oxide than those currently commercially available for use in the oxidation reaction.

These and other objects, aspects and advantages of this invention will be apparent to those skilled in the art from the following description.

SUMMARY OF THE INVENTION

In accordance with the invention a novel process for the preparation of predetermined olefin oxides and ketones from the corresponding olefin has been discovered, comprising reacting the selected olefin with an effective amount of thallic values, e.g., thallic oxide, $Tl_2O_3$, in an aqueous medium having present a large quantity of $CO_2$ and an absence of organic solvents and acids to produce the desired reaction products, which are then preferably extracted from the reaction system by absorption by supercritical $CO_2$ before they can hydrolyze to the corresponding glycol.

In combination with the above reaction, a process for the back oxidation and reuse of the thallic oxide which has been reduced to the thallous state in the prior reaction has also been employed, wherein the reduced thallous values, e.g. thallous bicarbonate and/or thallous carbonates and mixtures thereof from the olefin reaction are reacted with molecular oxygen in the presence of an effective catalyst for a predetermined time and temperature after having been first heated to drive off all the carbon dioxide present. The thallous values are substantially oxidized back to their thallic state, e.g., thallic oxide, which precipitates out of the solution, is filtered and recycled back to the first stage reactor, together with fresh thallic feed values to repeat the complete cycle of the process.

DETAILED DESCRIPTION OF THE INVENTION

The process of this invention is broadly applicable to a cyclical process for the formation of olefin oxides, ketones, and carbonates having from three to 30 carbon atoms from the reaction of the corresponding olefin and an excess of carbon dioxide in aqueous medium in the presence of thallic values, such as thallic oxide, $Tl_2O_3$.

The term "olefins", as used herein, includes substituted and unsubstituted aliphatic and alicyclic olefinically-unsaturated compounds which may be hydrocarbons or esters or alcohols or ketones or ethers or the like. Preferred compounds are those having from three to 30 carbon atoms. Illustrative olefins are propylene, normal butylene, isobutylene, the pentenes, the methyl pentenes, the normal hexenes, the octenes, the dodecenes, cyclohexene, methyl cyclohexene, butadiene, styrene, vinyl toluene, vinylcyclohexene, the phenyl cyclohexenes, and like hydrocarbon olefins, Olefins having halogen, oxygen, sulfur and like substituents can be used. Such substituted olefins are illustrated by allyl alcohol, methallyl alcohol, diallyl ether, methyl methacrylate, methyl oleate, allyl chloride, and the like. Propylene is the preferred olefin of choice; however, ethylene has been found to be substantially non-reactive in the process of the invention.

The amount of water present in the reaction zone can generally range from about 1 to 99 wt. % of the reactants, preferably from about 1 to 70%, and most preferably from 1 to 40%. The amount of reaction medium can be freely varied. Most preferably, however, enough is present to dissolve the thallic oxide and to provide a molar ratio of water to thallic oxide of at least 10 to 1, and preferably, about 500 to 1.

Carbon dioxide preferably will be supplied in its liquid state to the reaction zone and preferably is of such purity as that which is found in commercially available carbon dioxide. Nevertheless, minor amounts of impurities such as carbon monoxide may be tolerated. Inert gases such as nitrogen which do not affect the reaction may also be present in any reasonable amount, so long as the desired carbon dioxide pressure is provided. It is most preferably to the invention that there be present a large quantity of $CO_2$, e.g., that the molar ratio of carbon dioxide to water should be from about 10:1 to 1:1 but, most preferably, about 5:1 to 1:1. Higher amounts of $CO_2$ are equally operative but economically unnecessary while lesser amounts are believed to adversely affect reaction kinetics. It is also most preferred that $CO_2$ exist in the reaction vessel in its supercritical state, for ease in subsequent extraction of the product, particularly the olefin oxide. Without the use of supercritical $CO_2$ to extract the reaction products, not only is extraction made more difficult, but also the danger of the product subsequently hydrolyzing to the gylcol state is far greater.

While the presence of thallic values is critical to the invention, not all thallic values are equally useful, and thallic oxide ($Tl_2O_3$) is particularly preferred. However, the thallic salt of a weak acid, for example, an acetate, propionate, or butyrate may also be used. For purposes of this application the term "weak acid salt" refers to a salt which undergoes reaction conditions while providing a pH of about 2 to 10 and, most preferably, about 4 to 8. It has been found that thallic salts of strong acids, such as thallic chloride and thallic nitrate are substantially less effective in this form. Since the thallium is reduced from the thallic to the thallous state during the reaction the use of thallous components will be ineffective unless they can be effectively oxidized back to the thallic state.

It was desired to prepare a more catalytically active form of thallic oxide, $Tl_2O_3$ which, throughout the specification hereinafter will be intended as synonomous for thallic values, than presently available from the commercial sources, e.g., those sold under the "Aldrich" or "Alpha" trade name. Neutralization experiments of thallic chloride, nitrate and acetate using appropriate strong bases such as KOH, $NH_4OH$ and NaOH have produced thallic oxide precipitates. These solids were next dried in an oven at 90° C. and, particularly, in the case of thallic chloride with potassium hydroxide have produced a more active catalyst than those commercially available. Thallic oxide prepared by this method is preferably mixed with the thallic oxide produced from the back oxidation reaction of thallous values to thallic values and is charged as feed into the reactor along with the other reactants.

A substantial advantage of this process scheme is the absence of all organic solvents and acids in the process cycle, in sharp contrast to all currently available techniques which are known in the art. A significant problem with prior art processes has been the presence of solvents and acids which can be oxidized by molecular oxygen in the thallic regeneration back reactions, and which the present process eliminates.

The pH of the liquid reaction medium may vary widely, but it generally ranges from about 10 to less than about 3, preferably from about 9 to 5 and most preferably about 7–9. The foregoing pH values are those determined in the aqueous phase, where the reaction medium comprises a two phase system.

Although knowledge of the reaction by which olefin oxides and ketones are produced by the reaction of the corresponding olefin with carbon dioxide, thallic oxide, and water is not essential for a complete understanding of the invention, it may be helpful to set forth the apparent overall reaction, using propylene as the olefin of choice and thallic oxide as the oxidant.

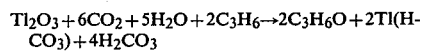
$$Tl_2O_3 + 6CO_2 + 5H_2O + 2C_3H_6 \rightarrow 2C_3H_6O + 2Tl(HCO_3) + 4H_2CO_3$$

The reaction can be carried out, in theory, at any convenient temperature, e.g., about room temperature to 150° C., but for best results, from the standpoint of an acceptable reaction rate, it is advantageous to undertake the reaction at moderate temperatures, e.g. to temperatures of about 50° to 120° C. and preferably about 80° to 110° C.

The reaction can be carried out in any reaction vessel or vessels into which the olefin, carbon dioxide, water and thallic oxide can be charged, and which will withstand the reaction operating pressures and temperatures. The reaction vessel should be provided with a suitable inlet for leading the olefin, such as propylene, from its source into the liquid reaction mixture, or, in the alternative, the reaction mixture can be pressured with the olefin to a desired predetermined temperature before introduction into the reaction vessel. The reaction can be carried out batch-wise or it can be run continuously. The olefin can be used in pure form or it can be diluted with an inert gas, e.g. nitrogen, argon, helium, or the like if so desired. The presence of a dilutant will, of course, make it necessary to employ a higher pressure to charge the equivalent olefin pressure. The pressure should be sufficient so as to insure that the carbon dioxide present will be in its supercritical state. It is generally advantageous to insure good contact between the reaction ingredients in the liquid reaction mixture, and for this purpose efficient agitation, e.g. such as a mechanical stirrer or an inert gas is suitably provided. The pressure in the reaction zone for the olefin oxidation can range from about 1 to 700 kg/cm$_2$, and preferably, from 80 to 350 kg/cm$_2$.

It is preferred that a two stage reactor set up be used in the process of the invention. It is envisioned that the first stage reactor will primarily undertake the oxidation of the olefin to its corresponding olefin oxide and ketone while concurrently reducing the thallic values, e.g. thallic oxide, to their thallous state. The second stage of the reactor scheme should preferably be used for the back oxidation of the formed thallous values back to their thallic state. It is most preferred that the reaction products of the olefin oxidation be extracted after the first stage reactor, preferably by supercritical carbon dioxide, and thereafter separated into the desired products or product. This is particularly advantageous since such an extraction has been shown to substantially eliminate hydrolysis of the formed olefin oxide to its undesired glycol state.

Alternatively, the product olefin oxide and ketone with lesser amounts of carbonates can be recovered from the reaction mixture by other conventional extraction techniques. In the case of propylene oxidation, acetone will be formed as a byproduct and can be separated from the propylene oxide in a conventional manner, e.g., by distillation.

A critical step in the instant process is the effective back oxidation of the thallous values to their original thallic state and their subsequent recycling to the reactor as product feed. In accordance with this invention, the monovalent thallium compounds, e.g., thallium carbonate and bicarbonate, are converted to a trivalent compound, e.g., thallic oxide, by first heating the thallous compound to drive off the carbon dioxide and then treating with molecular oxygen in the presence of a Group VIII noble metal catalyst, e.g., platinum, and in the presence of an effective support, e.g., α-alumina, for the catalyst in a fluid medium so as to oxidize the thallous compound to its thallic state in a rapid, effective and efficient manner. Conversions well above 50% are readily obtained, which is surprisingly achievable in a non-electrolytical environment.

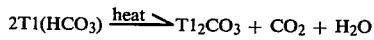

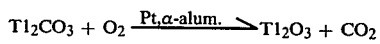

Such oxidation techniques have already been outlined in a variety of publications well known to those in the art, see, for example, the references cited in U.S. Pat. No. 4,192,814.

The Group VIII noble metals suitable for use comprise platinum, palladium, rhodium, ruthenium, osmium and iridium, but platinum, palladium, ruthenium and rhodium are preferred, especially platinum. Mixed catalysts can be used if desired. The catalyst is preferably used in a heterogenous system, e.g., in the form of a fixed bed over which the reaction medium is passed or in the form of a suspension. In the former case the catalyst is ordinarily supported upon a solid carrier, but it is also possible to use the catalyst in a homogenous system, i.e., it may be employed in a form which is soluble in the reaction medium. Thus, the Group VIII noble metal catalyst may be suitably added as a compound of the abovementioned metals, e.g., an oxide, preferably on a carrier, but it is most preferred to add the catalyst as the finely-divided metal, or as the metal supported on a carrier, e.g., platinum on α-alumina When the Group VIII noble metal catalyst is supported upon a carrier, the carrier or substrate which is employed is suitably in the form of a porous solid of such size that it can be readily dispersed in the liquid reaction medium, e.g., from 400 mesh/inch to ½ inch particle sizes. Such carrier materials are exemplified by pumice, alumina, silica, silica-alumina, megnesia, diatomaceous earth, bauxite, titania, zirconia, clays, both natural and acid treated such as Super-Filtrols, attapulgus (attapulgite), lime, magnesium silicate, silicon carbide, activated and unactivated carbons, zeolites as well as the zeolite molecular sieves, solid foams, such as ceramic honeycombs, and porous organic polymers. The above carriers are suitably used in the form of regular and irregular particles such as tubes, balls, broken pieces, and the like. Such supported forms of the Group VIII noble metals and their compounds are prepared by conventional methods, e.g., deposition from a solution, for example as described in U.S. Pat. No. 3,717,670 in connection with rhodium compounds and, indeed, many such supported catalysts are available commercially, particularly in the case of the zero valent free metal which is an effective form for use in this invention.

Concentrations of the Group VIII noble metals component on the support can vary widely, but illustrative concentrations lie within the range of 1 to 10 wt. %. Higher concentrations may, however, be used if desired.

The ratio of catalyst to the thallous values can also vary over a wide range. For example, 0.1 to 50 moles of catalyst per 100 moles of thallous components are preferably used, but lesser or greater amounts may be employed, if desired. The upper limit is determined only by economics and the lower limit only by the amount which will be catalytically effective.

The supports for the Group VIII noble metal catalyst in accordance with this invention can be any of those well known within the Group VIII noble metals catalytic art. In particular, α-alumina is the preferred support.

Ordinarily, the higher the reaction temperature, the greater is the back oxidation reaction rate. It is unnecessary, however, to employ very high temperatures and normally the reaction temperature will range from about 80° to about 250° C. Typically, temperatures of 100° to 200° C. are used, but higher or lower temperatures can also be operable; at excessively high temperatures undesired decomposition reactions may occur.

Total pressure is not a significant parameter of back oxidation process, and atmospheric or superatmospheric pressures can be employed. However, it is desirable to have oxygen partial pressures above the reaction mixture of at least 50 to 1500 kg/cm$^2$.

The reaction medium for the conversion of thallous to thallic values will be a substantially aqueous system. When water is present in the absence of any significant organic solvents and acids, the thallic values produced will normally be converted into the desired thallium form, e.g., $Tl_2O_3$.

The thallic values formed as a result of the back oxidation reaction are preferably combined with a second source of thallic values, e.g., the catalytically active thallic oxide, and are recycled back into the first stage of the reactor system and mixed with the other reactants, e.g. water, carbon dioxide and the desired olefin to be oxidized.

In a narrower embodiment of the invention, a surprising chemical reaction has been discovered in which the production of a desired olefin oxide and ketone from the corresponding olefin is generated in an aqueous, carbon dioxide environment free from organic solvents and acids. Although it is not desired to be bound by theory, it is believed that such a reaction occurs via a two step reaction mechanism. In the first, rate determining, equilibrium step, a thallic bicarbonate is formed. In a second, fast step, using propylene as an example, a hydroxythallation intermediate is formed which rapidly decomposes to thallous bicarbonate and propylene oxide.

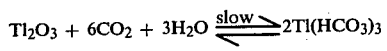

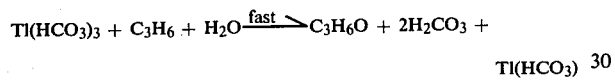

It is believed that the ratio of water to carbon dioxide present is an important factor in this reaction, since the ratio is believed to substantially determine the rate at which the slow reaction approaches equilibrium. The well known equilibrium between $CO_2$, $H_2O$ and carbonic acid, e.g.;

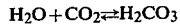

heavily favors the left side of the equilibrium at normal temperatures and pressures. However, excess quantities present of carbon dioxide will shift the equilibrium to the right and form a larger concentration of carbonic acid. The pH of carbonic acid should range from about 3 to 4. The presence of carbonic acid is believed to permit the solubilization of the oxidizing thallium compounds, e.g., thallic oxide, in the form of the desired thallic bicarbonate, $Tl(HCO_3)_3$, followed by the subsequent reaction of this bicarbonate with the olefin to form the desired olefin oxide and ketone. In effect, the carbon dioxide and water serve to activate the thallic oxide or other thallic-containing oxidizing agent.

After completion of the reaction and formation of the desired products, it is next desired to both remove the olefin oxide and ketone products from the reaction zone and while doing so, prohibit the formation of any significant amount of the corresponding glycol.

Carbon dioxide in its supercritical state, e.g., where it exists as a one phase fluid occurring above both a critical temperature and pressure, Tc and Pc, which is 31° C. and 75.3 kg/cm² for $CO_2$, is well known as an extremely good extractant. Carbon dioxide in the supercritical state is capable of quickly extracting the formed olefin oxide and ketone into the carbon dioxide phase, thus preventing the competing hydrolysis reaction of the epoxide to the corresponding glycol from occurring. $CO_2$ is preferably quickly removed from the reactor and the reaction products are subsequently separated from it by conventional extractive techniques.

Another significant aspect of the invention is a substantial ability to influence the selectivity of the reaction product, which can be important since frequently either the olefin oxide or the ketone, usually the oxide, but not both, may be the desired end product. The following examples are provided to illustrate the invention in accordance with the principles of this invention but are not construed as limiting the invention in any way except as indicated by the appended claims.

EXAMPLE 1

Thallic oxide was prepared from the neutralization of thallic chloride by potassium hydroxide in an aqueous solution having a pH of 7 as measured by a pH meter. The insoluble thallic oxide precipitate which formed was filtered and washed well with de-ionized water. The resultant oxide was then dried in an oven at 90° C. for 12 hours.

4.0 g thallic oxide (8.8 mmoles) and 30 g water (1.7 moles) were added to a 300 cc Autoclave Engineers stainless steel Magnedrive Autoclave. The autoclave was cooled to −78° C. and 40 g propylene (0.95 mole) and 100 g carbon dioxide (2.3 mole) were introduced. The autoclave was then heated to 100° C. for 1.0 hour to reach a total pressure of 196.8 kg/cm². The autoclave volatiles were then vented into a methyl ethyl ketone solution followed by a 0.10 M megnesium chloride-hydrochloric acid scrubber which trapped the propylene oxide. The excess hydrochloric acid was titrated with 0.10 M sodium hydroxide. The organics remaining in the aqueous solution were measured by standard gas chromatographic techniques. The analysis showed 1.01 mmoles propylene oxide (48% yield), 0.71 mmoles acetone (34% yield) and 0.10 mmoles propylene carbonate (5% yield). 2.1 mmoles of thallous bicarbonate (24% conversion) were detected in the water solution by atomic absorption techniques. The pH of the solution was measured to be 8.1. The yields of oxidized propylene products in this and the following examples are based on the thallic compounds reduced to the thallous state. The conversions of thallic reduction to thallous are based on the starting quantity of thallic compound.

EXAMPLE 2

The identical reaction of Example 1 was reported in the absence of any carbon dioxide. The analyses showed that no detectable propylene oxide and only 0.12 mmoles acetone (13% yield) formed. The pH of the solution was 8.1, and 0.9 mmole of thallous hydroxide (10% conversion) was measured in solution.

EXAMPLE 3

Still another run identical to Example 1 was made except for the introduction of 141 g carbon dioxide (3.2 moles). The autoclave was heated to 100° C. for 1.0 hour to reach a pressure of 288.2 kg/cm². The analyses showed 1.30 mmoles propylene oxide (59% yield), 0.70 mmoles acetone (32% yield) and 0.12 mmoles propylene carbonate (5% yield). The pH of the solution was 8.2 and 2.2 mmoles (25% conversion) of thallous bicarbonate were formed.

EXAMPLE 4

Thallic oxide was prepared by the method of Example 1. 4.0 g thallic oxide (8.8 mmoles) and 30 g water then added to the autoclave of Example 1. The autoclave was cooled to −78° C. and 20 g propylene (0.48 mole) and 168 g carbon dioxide (3.8 moles) were added. The autoclave was heated to 100° C. for 1.0 hours to produce a total pressure of 274.2 kg/cm$^2$. Analysis showed 0.80 mmoles propylene oxide (57% yield), 0.54 mmoles acetone (39% yield) and a trace of propylene carbonate. 1.40 mmoles thallous bicarbonate (16% conversion) was detected in solution, and the pH was 7.8.

EXAMPLE 5

In this example, the effect of an increase in the water concentration was observed.

Thallic oxide was again prepared as described in Example 1. 4.0 g thallic oxide (8.8 mmoles) and 120 g of water (6.8 moles) were added to the autoclave in Example 1, cooled to −78° C., and 40 g propylene (0.95 mole) and 87 g carbon dioxide (2.0 mole) were then introduced. The autoclave was heated to 100° C. for 1.0 hours to produce a total pressure of 232.0 kg/cm$^2$. The analysis 2 showed 0.4 mmoles propylene oxide (7% yield) and 1.61 mmoles acetone (28% yield). The pH was 7.8, and 5.7 mmoles of thallous bicarbonate (65% conversion) were detected in solution.

EXAMPLE 6

This example is a further study of the effect of an increase in the water concentration.

Thallic oxide was prepared as described in Example 1. 4.0 g thallic oxide (8.8 mmoles) and 60.0 g water (3.4 moles) were added to the autoclave of Example 1. 40 g propylene (0.95 mole) and 95 g carbon dioxide (2.2 moles) were added and the solution was heated to 100° C. for 1.0 hours to give a total pressure of 165.2 kg/cm$^2$. The analysis showed 0.67 mmoles propylene oxide (18% yield) 1.62 mmoles acetone (43% yield) and 0.08 mmoles propylene carbonate (2% yield). 3.73 mmoles of thallous bicarbonate (42% conversion) were detected in solution, and the pH was measured as 8.0.

EXAMPLE 7

This example tests the effect of a lower concentration of thallic oxide.

Thallic oxide was again prepared as described in Example 1. 2.0 g thallic oxide (4.4 mmoles), 30.0 g water (1.7 moles) 40 g propylene (1.0 moles), and 101 g of carbon dioxide (2.3 moles) were added to the autoclave of Example 1. The autoclave was heated to 100° C. for 1.0 hours to produce a total pressure of 168.7 kg/cm$^2$. The analysis detected 0.65 mmoles propylene oxide (31% yield), 0.64 mmoles acetone (30% yield) and 0.16 mmoles propylene carbonate (8% yield). 2.1 mmoles of thallous bicarbonate (48% conversion) was detected in a solution having a pH of 7.5.

EXAMPLE 8

This example tests the effect of a different method of preparation of thallic oxide from that of Example 1.

Thallic oxide was prepared by neutralization of thallic nitrate with potassium hydroxide in an aqueous solution having a pH of 7. The resultant thallic oxide was filtered and washed well with water. 4.0 g of thallic oxide (8.8 mmoles), 30.0 g water (1.7 moles), 40 g propylene (0.95 moles) and 96 g carbon dioxide (2.2 moles) were then added to the autoclave in Example 1 which was subsequently heated to 100° C. for 1.0 hours. The analysis detected 0.05 mmole propylene oxide (2% yield) and 0.44 mmole acetone (21% yield). 2.1 mmoles of thallous bicarbonate (24% conversion) was in solution and pH =8.5.

EXAMPLE 9

This example tests the effect of another method of preparation of thallic oxide.

Thallic oxide was prepared by neutralization of thallic chloride with sodium hydroxide in an aqueous solution to a pH of 7. The resultant insoluble thallic oxide precipitate was then washed well with water.

4.0 g thallic oxide (8.8 mmoles), 30.0 g water (1.7 moles), 40 g propylene (0.95 mole) and 96 g carbon dioxide (2.2 moles) were added to the autoclave, which was subsequently heated to 100° C. for 1.0 hour. The analysis detected 0.17 mmole propylene oxide (16% yield), 0.56 mmole acetone (52% yield), and 0.06 mmole propylene carbonate (6% yield). 1.07 mmoles thallous bicarbonate (12% conversion) was detected at pH =8.0.

EXAMPLE 10

This example shows the effect of the use of a commercial Aldrich 99.999% thallic oxide sample.

4.0 thallic oxide (8.8 mmoles), 30.0 g water (1.7 moles), 40 g propylene (0.95 mole) and 102 g carbon dioxide (2.3 moles) were added to the autoclave in Example 1 which was subsequently heated to 100° C. for 1.0 hours. The analysis showed 0.30 mmoles propylene oxide (12% yield) and 0.44 mmoles acetone (17% yield). 2.60 mmoles thallous bicarbonate (30% conversion) was detected in solution at pH =8.3.

EXAMPLE 11

This example tests the effect of a platinum cocatalyst in solution.

Thallic oxide was prepared as in Example 1. 4.0 g thallic oxide (8.8 mmoles), 1.2 g 5% platinum on α-alumina (0.3 mmole platinum), 30.0 g water (1.7 mole) 40 g propylene (1.0 mole) and 105 g carbon dioxide (2.4 mole) were added to the autoclave in Example 1 which was subsequently heated to 100° C. for 1.0 hours. The analysis detected 0.90 mmole propylene oxide (35% yield), 0.74 mmole acetone (29% yield) and 0.20 mmole propylene carbonate (8% yield). 2.54 mmoles of thallous bicarbonate (29% conversion) were detected in solution at a pH of 8.0.

The following examples demonstrate the reoxidation of the reduced thallous to thallic to complete the cyclic process.

EXAMPLE 12

The unreacted insoluble thallic oxide present after the propylene oxidation in Example 1 was filtered, and the water solution containing thallous bicarbonate (2.1 mmoles) was boiled for 0.5 hour to expel the carbon dioxide. The solution was then subjected to 56.2 kg/cm$^2$ oxygen at 180° C. in a second autoclave for 1.0 hour. Iodometric analysis of the formed insoluble thallic oxide which formed indicated a 48% back conversion to thallic. An atomic absorption analysis of the remaining thallous carbonate in solution confirmed the analysis. The thallic oxide from this oxidation is combined with that remaining from Example 1, and the propylene oxidation reaction is repeated.

EXAMPLE 13

This example tests the effect of a platinum cocatalyst in the thallous oxidation.

The unreacted thallic oxide from the propylene oxidation, as in Example 1 was filtered and 30.0 g of a water solution of thallous bicarbonate (2.8 mmoles) was boiled for 0.5 hour to expel the carbon dioxide. The solution was then subjected to 56.2 kg/cm² of molecular oxygen pressure at 120° C. for 2.0 hour in the presence of 0.6 g 5% platinum on an α-alumina support (0.15 mmoles). A 90% conversion to thallic oxide was obtained. Only 0.3 mmole of thallous bicarbonate was detected remaining in solution. The insoluble thallic oxide and the platinum on α-alumina catalyst were reused for propylene oxidation as in Example 11.

EXAMPLE 14

This example tests the effect of carbon dioxide on the thallous carbonate oxidation by molecular oxygen.

Example 13 was repeated except that the solution wasn't boiled for 0.5 hour to expel the carbon dioxide. A 14% conversion to thallic oxide was obtained.

EXAMPLE 15

This example tests the effect of another support for platinum.

The unreacted thallic oxide from the propylene oxidation was filtered, and the 30.0 g water solution of thallous bicarbonate (2.8 mmoles) was boiled for 0.5 hour to expel the carbon dioxide. The solution was then subjected to 56.2 kg/cm² oxygen at 120° C. for 2.0 hours in the presence of 0.6 g 5% platinum on α-alumina (0.15 mmole). A 23% conversion to thallic oxide was obtained.

The next two examples show the effect of different reaction temperatures:

EXAMPLE 16

Thallic oxide was again prepared as in Example 1. 4.0 g of thallic oxide (8.8 mmoles), 30 g water (1.7 moles), 80 g propylene (1.9 moles) and 95 g carbon dioxide (2.2 moles) were added to the autoclave in Example 1 which was then heated to 70° C. for 2.0 hours. The analysis showed 0.81 mmoles propylene oxide (58% yield), 0.55 mmoles acetone (39% yield) and 0.06 mmoles propylene carbonate (4% yield) to have formed. 1.40 mmoles of thallous bicarbonate (16% conversion) was detected in a solution having a pH =7.9.

EXAMPLE 17

Thallic oxide was again prepared as in Example 1. 2.0 g of thallic oxide (4.4 mmoles), 30 g water (1.7 moles), 80 g propylene (1.9 moles), and 98 g carbon dioxide (2.2 moles) were added to the autoclave in Example 1, which was subsequently heated to 50° C. for 2.0 hours. The analysis showed the formation of 0.31 mmoles of propylene oxide (52% yield) and 0.27 mmole of acetone (45% yield). 0.60 g of thallous bicarbonate (14% conversion) was detected in solution at pH =7.1.

I claim:

1. A process for converting an olefin to its corresponding olefin oxide comprising:
reacting a mixture of the olefin, carbon dioxide, a thallic compound and water in a substantially organic solvent-free, acid-free reaction zone to form the olefin oxide and a thallous compound;
separating and collecting the formed olefin oxide product from the reaction mixture.

2. A process as claimed in claim 1 wherein the olefin is propylene.

3. A process as claimed in claim 1 wherein the olefin oxide formed is propylene oxide.

4. A process as claimed in claim 1 wherein the thallic compound is thallic oxide and the thallous compound is thallous bicarbonate.

5. A process as claimed in claim 1 wherein the mole ratio of $H_2O/CO_2$ is about 1:1 to 1:5.

6. A process as claimed in claim 1 wherein the reaction zone temperature ranges from about 50° to 120° C.

7. A reaction as claimed in claim 1 wherein the reaction zone pressure ranges from about 80 to about 350 kg/cm₂.

8. A process for converting propylene to propylene oxide comprising:
reacting a gaseous mixture of propylene and supercritical carbon dioxide with thallic oxide in an aqueous, non-organic solvent, non-acid medium at a temperature of about 80° to 110° C. according to the following reaction:

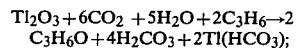
$$Tl_2O_3 + 6CO_2 + 5H_2O + 2C_3H_6 \rightarrow 2 C_3H_6O + 4H_2CO_3 + 2Tl(HCO_3);$$

the ratio of $CO_2/H_2O$ being from about 1:1 to 5:1.

9. A process for the production of olefin oxides comprising:
(a) contacting a mixture of an olefin, carbon dioxide, a thallic compound and water in a substantially organic solvent-free, acid-free reaction zone to form an olefin oxide and a thallous compound;
(b) withdrawing a first stream from the reaction zone, the stream comprising the formed olefin oxide, separating and collecting the olefin oxide, from the first stream;
(c) heating the mixture of thallous values to drive off the carbon dioxide present;
contacting the thallous values present in the mixture with molecular oxygen and an effective catalyst at 80° to 250° C. so as to oxidize the thallous values back to their thallic form;
separating and recycling back to the reaction mixture the regenerated thallic values.

10. A process as claimed in claim 9 wherein the olefin is propylene.

11. A process as claimed in claim 9 wherein the olefin oxide formed is propylene oxide.

12. A process as claimed in claim 9 wherein the thallic compound is thallic oxide and the thallous compounds are thallous bicarbonate and thallous carbonate.

13. A process as claimed in claim 9 wherein the mole ratio of $H_2O/CO_2$ is about 1:1 to 1:5.

14. A process as claimed in claim 9 wherein the front reaction temperature ranges from about 50° to 120° C.

15. A process as claimed in claim 9 wherein the first reaction zone pressure ranges from about 80 to about 350 kg/cm².

16. A process as claimed in claim 9 wherein the. olefin oxide product is extracted from the reaction mixture by supercritical $CO_2$.

17. A process as claimed in claim 9 wherein an effective catalyst for oxidizing thallous values to thallic oxide is platinum on an α-alumina support.

18. A process as claimed in claim 9 wherein the fresh thallic oxide supplied to the reaction mixture is prepared from the product of the neutralization reaction of thallic anions with their corresponding base.

19. A process as claimed in claim 9 wherein the thallous values are back oxidized to $Tl_2O_3$ according to the reaction equation:

$$2Tl(HCO_3) \xrightarrow{heat} Tl_2CO_3 + CO_2 + H_2O$$

-continued $$Tl_2CO_3 + O_2 \xrightarrow{Pt,\alpha\text{-alum}} Tl_2O_3 + CO_2$$

20. A process as claimed in claim 1 whereiin the amount of water present is about 1–70 wt % of the reaction zone mixture.

21. A process as claimed in claim 9 wherein the amount of water present is about 1–70 wt % of the reaction zone mixture.

* * * * *